United States Patent
Isobe et al.

(10) Patent No.: US 8,960,006 B2
(45) Date of Patent: Feb. 24, 2015

(54) ULTRASONIC INSPECTION APPARATUS, ULTRASONIC PROBE APPARATUS USED FOR ULTRASONIC INSPECTION APPARATUS, AND ULTRASONIC INSPECTION METHOD

(75) Inventors: Hideo Isobe, Tokyo (JP); Takahiro Ikeda, Yokosuka (JP); Ryoichi Arai, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 781 days.

(21) Appl. No.: 12/679,115

(22) PCT Filed: Sep. 18, 2008

(86) PCT No.: PCT/JP2008/066819
§ 371 (c)(1),
(2), (4) Date: Mar. 19, 2010

(87) PCT Pub. No.: WO2009/038113
PCT Pub. Date: Mar. 26, 2009

(65) Prior Publication Data
US 2010/0212429 A1    Aug. 26, 2010

(30) Foreign Application Priority Data

Sep. 21, 2007 (JP) ................................ 2007-244910
Sep. 8, 2008 (JP) ................................ 2008-230054

(51) Int. Cl.
*G01N 29/06* (2006.01)
*G01N 29/24* (2006.01)

(52) U.S. Cl.
CPC .......... *G01N 29/069* (2013.01); *G01N 29/2437* (2013.01); *G01N 2291/011* (2013.01); *G01N 2291/0231* (2013.01); *G01N 2291/0289* (2013.01)
USPC .................... 73/602; 73/625; 73/626; 73/628

(58) Field of Classification Search
CPC ............ G01N 29/069; G01N 29/2437; G01N 2291/011; G01N 2291/0231; G01N 2291/0289
USPC .................................... 73/602, 625, 626, 628
See application file for complete search history.

(56) References Cited

U.S. PATENT DOCUMENTS 4,525,790 A * 6/1985 Nakamura .................... 702/124
4,866,614 A * 9/1989 Tam .............................. 600/437

(Continued)

FOREIGN PATENT DOCUMENTS

| JP | 61-146237 | 7/1986 |
| JP | 3-20665 | 1/1991 |

(Continued)

OTHER PUBLICATIONS

International Preliminary Report on Patentability and Written Opinion issued by the International Bureau of WIPO on Apr. 7, 2010, for International Application No. PCT/JP2008/066819.

(Continued)

*Primary Examiner* — Lisa Caputo
*Assistant Examiner* — Rose M Miller
(74) *Attorney, Agent, or Firm* — Finnegan, Henderson, Farabow, Garrett & Dunner, L.L.P.

(57) ABSTRACT

An ultrasonic inspection apparatus includes: an ultrasonic probe apparatus including an ultrasonic transducer; a drive element selecting section that selects a required piezoelectric vibrator of the ultrasonic transducer; a signal detecting circuit that detects an electric signal dependent on a reflected echo of an ultrasonic wave emitted from the selected piezoelectric vibrator; a signal processing section that produces data on an internal image of the inspection object based on the detected reflected echo; a second display unit that combines multiple pieces of image data acquired from the signal processing section and displays an integrated visualization data result; and an second input unit that is used to perform an operation command such as a command input to start or terminate an inspection or an a command to set inspection condition.

15 Claims, 4 Drawing Sheets

(56) References Cited

U.S. PATENT DOCUMENTS

| | | | |
|---|---|---|---|
| 6,540,681 B1 * | 4/2003 | Cheng et al. | 600/443 |
| 2001/0052264 A1 * | 12/2001 | Johnson et al. | 73/628 |
| 2002/0134133 A1 * | 9/2002 | Ogawa | 73/1.86 |
| 2004/0024320 A1 | 2/2004 | Karasawa et al. | |
| 2005/0102009 A1 * | 5/2005 | Costantino | 607/96 |

FOREIGN PATENT DOCUMENTS

| | | | | |
|---|---|---|---|---|
| JP | 2733311 B | * | 1/1991 | |
| JP | 8-122309 | | 5/1996 | |
| JP | 08122309 A | * | 5/1996 | |
| JP | 9-26417 | | 1/1997 | |
| JP | 2733311 | | 12/1997 | |
| JP | 2003-149213 | | 5/2003 | |
| JP | 2004-53360 | | 2/2004 | |
| JP | 2004053360 A | * | 2/2004 | |
| JP | 2006-317417 | | 11/2006 | |
| JP | 2006317417 A | * | 11/2006 | |
| JP | 3961359 | | 5/2007 | |

OTHER PUBLICATIONS

International Search Report from the Japanese Patent Office for PCT International Application No. PCT/JP2008/066819, mailed Dec. 16, 2008.

Search Report and Written Opinion issued by the Intellectual Property Office of Singapore on Jun. 9, 2014, for Singapore Application No. 2012069787.

* cited by examiner

ULTRASONIC INSPECTION APPARATUS, ULTRASONIC PROBE APPARATUS USED FOR ULTRASONIC INSPECTION APPARATUS, AND ULTRASONIC INSPECTION METHOD

CROSS-REFERENCE TO RELATED APPLICATIONS

This application is a national phase application of International Application No. PCT/JP2008/066819, filed Sep. 18, 2008, and claims the priority of Japanese Application Nos. 2007-244910, filed Sep. 21, 2007, and 2008-230054, filed Sep. 8, 2008, the contents of all of which are incorporated herein by reference.

TECHNICAL FIELD

The present invention relates to an ultrasonic inspection technique for inspecting, in a non-destructive manner, an internal structure, a flaw state or a state of a junction of an object to be inspected by using ultrasonic waves, and more particularly, to an ultrasonic inspection apparatus which visualizes a state of flaw, peel-off or void, or an unstuck state of a junction in an interior of an object to be inspected, and to an ultrasonic probe apparatus used in the ultrasonic inspection apparatus and to an ultrasonic inspection method.

BACKGROUND ART

Examples representing this type of ultrasonic inspection technique include ultrasonic inspection apparatuses disclosed in Japanese Patent Laid-Open Nos. 2003-149213 (Patent Document 1), 2004-53360 (Patent Document 2), 2006-317417 (Patent Document 3) and 8-122309 (Patent Document 4).

Such ultrasonic inspection apparatus includes an ultrasonic transducer having multiple piezoelectric transducer elements (piezoelectric vibrators) arranged in a plane in a matrix or an array (linear shape), and the internal structure or a state of flaw (defect), void, oxide film, peel-off or the like of an object to be inspected is visualized by using ultrasonic waves transmitted from or received by the ultrasonic transducer to thereby inspect the object without destructing the object.

Generally, the main body of the ultrasonic inspection apparatus and the ultrasonic transducer are connected through a signal cable of a length of several meters. When an object is inspected by using such ultrasonic inspection apparatus, the operator (inspector) using the ultrasonic inspection apparatus must perform the ultrasonic inspection by checking a display of a display unit included in the ultrasonic inspection apparatus, which is apart in location from an inspection position of the inspection object, while carrying out accurate alignment of the ultrasonic transducer and proper scanning on the surface of the inspection object.

The operation for accurate position adjustment, scanning and the like of the ultrasonic transducer requires due attention. In using the ultrasonic inspection apparatus, it is very difficult for the operator (inspector) to manipulate the ultrasonic transducer while checking a display of the display unit included in the main body of the ultrasonic inspection apparatus placed apart from the inspection object (object to be inspected). Further, when the display unit is placed close to the inspection object, the operator (inspector) using the ultrasonic inspection apparatus must alternately watch the ultrasonic transducer and the display unit to manipulate the ultrasonic transducer and also to check a display of the display unit. Thus, it was difficult to solve the complex and difficult in basic operations or workings.

Particularly, when the operator (inspector) using the ultrasonic inspection apparatus inspects an object by manually manipulating the ultrasonic transducer, it takes much labor to obtain proper and accurate inspection results. Accordingly, the inspection using the ultrasonic inspection apparatus is not always easy.

Then, as conventional technology, there has been known an ultrasonic inspection apparatus in which a display unit and a switch for switching images displayed in the display unit are integrally arranged in an ultrasonic probe apparatus with an ultrasonic transducer (for example, Patent Document 4).

In a conventional ultrasonic inspection apparatus, there is utilized an ultrasonic transducer which is constituted of a piezoelectric transducer section including multiple piezoelectric transducer elements. When an inspection object is inspected using the conventional ultrasonic inspection apparatus, the operator must manipulate the ultrasonic transducer while checking a display of the display unit included in the main body of the conventional ultrasonic inspection apparatus.

For example, with the conventional ultrasonic inspection apparatus, when an inspection is performed by scanning the surface of an inspection object with the ultrasonic transducer, the ultrasonic transducer and the display unit included in the main body must be alternately watched with much labor to manipulate the ultrasonic transducer and also check a display of the display unit. As a result, there may cause a case where the scanning position of the ultrasonic transducer is displaced during the checking of the display unit, or because of excessive attention paid to the ultrasonic transducer, the operator continues the working without noticing an abnormal display of the display unit. That is, in the ultrasonic inspection using an ultrasonic transducer for inspecting an object, the operator usually must check a state displayed by the display unit visualizing the internal structure or a state of flaw, void, oxide film, peel-off or the like of the object to be inspected, and perform the scanning by the ultrasonic transducer while feeding back the checked state. However, such task or working was difficult for the conventional ultrasonic probe apparatus.

Accordingly, it is difficult to inspect an internal state of an inspection object efficiently and accurately using the ultrasonic inspection apparatus in a field or manufacturing process site.

Furthermore, in the conventional ultrasonic inspection apparatus, a display unit and a switch for switching images displayed in a display unit are integrally arranged in an ultrasonic probe apparatus provided with an ultrasonic transducer, so that the operator can cause the ultrasonic transducer to scan while checking images displayed on the display unit. In this case, however, in order to start or terminate the inspection with the ultrasonic probe apparatus disposed at a desired position, it is necessary for the operator to input a command to start or terminate an inspection while viewing images in the display unit. Furthermore, in order to make an inspection object to an image capable of being properly inspected, it is necessary for the inspection conditions of the ultrasonic inspection apparatus to be properly changed or selected.

DISCLOSURE OF THE INVENTION

The present invention was conceived in consideration of the circumstances mentioned above and an object thereof is to provide an ultrasonic inspection apparatus in which an ultrasonic probe apparatus provided with an ultrasonic transducer can be easily manipulated in a field or manufacturing process site so as to inspect an internal flaw, peel-off or void, or an unstuck junction of an object to be inspected efficiently and accurately, to provide an ultrasonic probe apparatus used in the ultrasonic inspection apparatus, and also to provide an ultrasonic inspection method.

Another object of the present invention is to provide an ultrasonic inspection apparatus in which an ultrasonic probe apparatus is separated from the main body of the ultrasonic inspection apparatus and downsized or made compact so that the ultrasonic inspection apparatus is portable and also provide the ultrasonic probe apparatus used in the ultrasonic inspection apparatus.

An ultrasonic inspection apparatus according to the present invention comprises, in order to achieve the above objects: an ultrasonic probe apparatus provided with an ultrasonic transducer constituted of a plurality of piezoelectric vibrators; a drive element selecting section that is connected to the plurality of piezoelectric vibrators of the ultrasonic transducer and is adopted to select a required piezoelectric vibrator based on a drive signal from a signal generator; a signal detecting circuit that causes an ultrasonic wave emitted from the piezoelectric vibrator selected by the drive element selecting section to be incident via an acoustic propagation medium on an inspection object and receives a reflected echo thereof to detect an electric signal dependent on the reflected echo; and a signal processing section that applies a parallel arithmetic process to the detected electric signal dependent on the reflected echo and produces data on an internal image of the inspection object, wherein the ultrasonic probe apparatus includes a display unit that displays an image based on the image data produced by the signal processing section, and an input unit used to input an operation command such as a command to start or terminate an inspection, or to set inspection conditions.

An ultrasonic probe apparatus, according to the present invention, connected to a main body of an ultrasonic inspection apparatus, comprises, in order to achieve the above objects: a probe holder in a shape of a box; an ultrasonic transducer including a plurality of piezoelectric vibrators incorporated in the probe holder; a display unit incorporated in the probe holder; and an input unit incorporated in the probe holder, wherein the ultrasonic transducer, the display unit and the input unit are integrally assembled within the probe holder.

An ultrasonic inspection method according to the present invention comprises the steps of, in order to achieve the above objects:

preparing an ultrasonic inspection apparatus including: an ultrasonic probe apparatus including the ultrasonic transducer constituted of a plurality of piezoelectric vibrators, a display unit which displays an image based on image data produced by a signal processing section, and an input unit used to perform an operation command such as a command to start or terminate an inspection or to set an inspection condition; a drive element selecting section which is connected to a plurality of piezoelectric vibrators of the ultrasonic transducer and selects a required piezoelectric vibrator based on a drive signal from a signal generator; a signal detecting circuit which causes an ultrasonic wave emitted from the piezoelectric vibrator selected by the drive element selecting section to be incident via an acoustic propagation medium on the inspection object and receives a reflected echo thereof to detect an electric signal dependent on the reflected echo; and a signal processing section which applies a parallel arithmetic process to the detected electric signal dependent on the reflected echo and produces data on an internal image of the inspection object;

disposing the ultrasonic probe apparatus at a predetermined inspection position of the inspection object;

inputting a command to set inspection conditions through the input unit;

repeating an arrangement of the ultrasonic probe apparatus and an input setting of the command to set the inspection conditions through the input unit until a predetermined display is obtained in the display unit;

inputting an inspection start command through the input unit after adjustment of the display of the display unit;

inspecting the inspection object for flaws by causing the ultrasonic probe apparatus to scan a predetermined range of the inspection object; and inputting an inspection terminate command through the input unit after completion of inspecting the predetermined range of the inspection object.

According to the ultrasonic inspection apparatus, the ultrasonic probe apparatus used in the ultrasonic inspection apparatus and the ultrasonic inspection method according to the present invention, an internal flaw, peel-off or void, or an unstuck junction of an inspection object can be inspected efficiently and accurately by easily manipulating the ultrasonic probe apparatus including the ultrasonic transducer in the field or the manufacturing process site.

BRIEF DESCRIPTION OF THE DRAWINGS

FIG. 2 is a view schematically illustrating the configuration of an exemplary probe holder constituting an ultrasonic probe apparatus of the ultrasonic inspection apparatus according to the present invention, in which FIG. 2 (A) is a plan view, FIG. 2 (B) is a front view and FIG. 2 (C) is a side view.

BEST MODE FOR CARRYING OUT THE INVENTION

An ultrasonic inspection apparatus, an ultrasonic probe apparatus used in the ultrasonic inspection apparatus and an ultrasonic inspection method according to the present invention will be described hereunder with reference to FIGS. 1 to 4.

Figure 1:
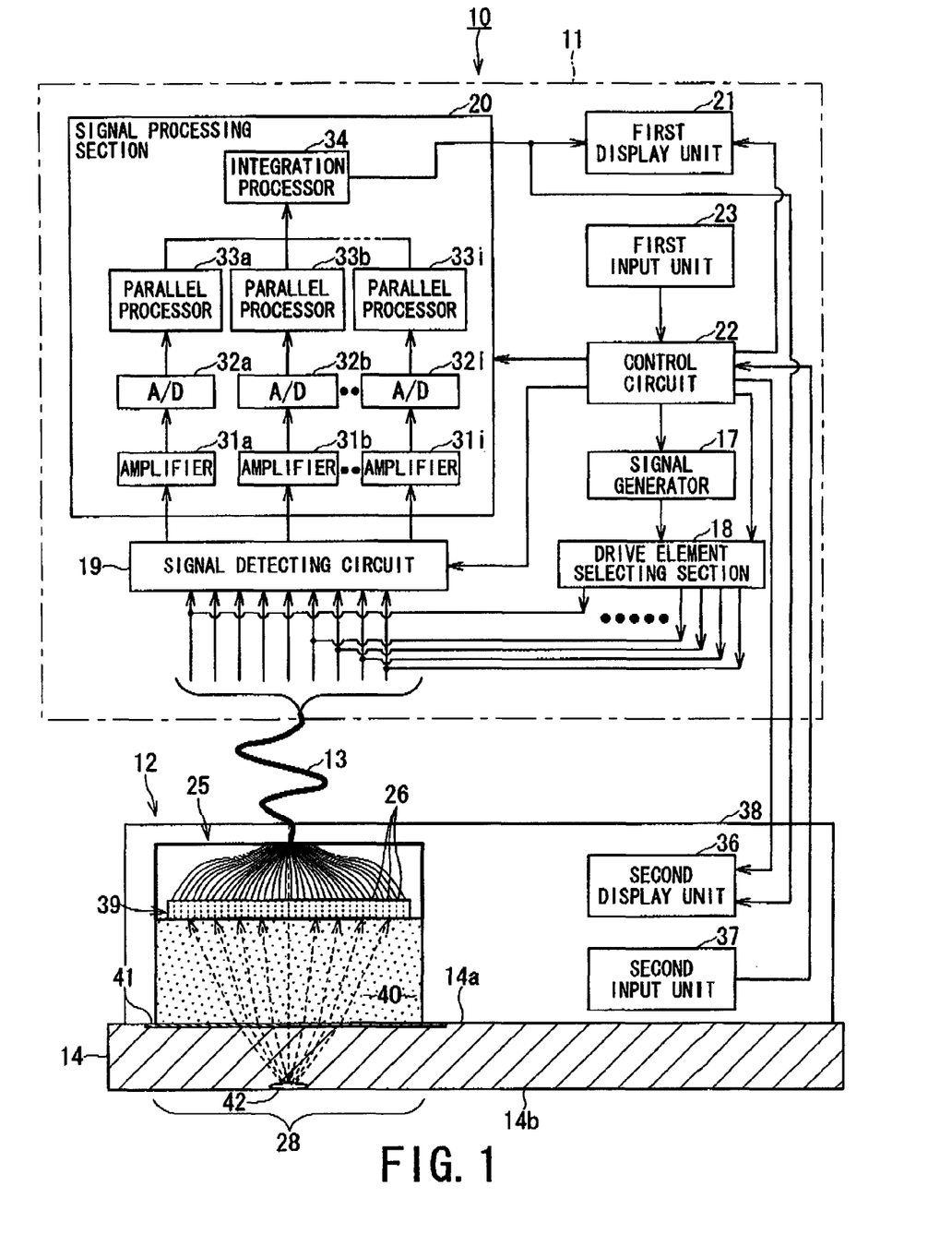
FIG. 1 is a view schematically illustrating a whole configuration of an ultrasonic inspection apparatus according to the present invention.

FIG. 1 is a view schematically illustrating the whole configuration of an ultrasonic inspection apparatus according to the present invention.

An ultrasonic inspection apparatus 10 includes an apparatus body 11 and an ultrasonic probe apparatus 12 constructed so as to be portable and of a handy type. The apparatus body 11 and the ultrasonic probe apparatus 12 are separately disposed and connected to each other via a flexible signal cable 13. The ultrasonic inspection apparatus 10 has a function as an ultrasonic camera which can finely image the internal structure or a flawed configuration of an object to be inspected (called inspection object or inspected object, hereinafter) 14.

Weight and portability of the ultrasonic probe apparatus 12 will be described with an example. The ultrasonic probe apparatus 12 is of a palm size and equal to or less than 1 kg, more specifically, weighs several hundred grams. The ultrasonic probe apparatus 12 has a size, shape and weight which allow the operator (inspector) to grip the ultrasonic probe apparatus 12 and perform manual scanning.

The apparatus body 11 constituting the ultrasonic inspection apparatus 10 includes a signal generator 17, a drive element selecting section 18, a signal detecting circuit 19, a signal processing section 20, a first display unit 21, a control circuit 22 and a first input unit 23.

The signal generator 17 produces a drive signal which drives an ultrasonic transducer (ultrasonic sensor) 25 included in the ultrasonic probe apparatus 12.

The drive element selecting section 18 selects a drive signal from the signal generator 17 and selectively drives a piezoelectric vibrator (piezoelectric transducer element) 26 of the ultrasonic transducer 25.

The signal detecting circuit 19 detects, as an electric signal, a reflected echo from an inspection region (target region) 28 through the ultrasonic transducer 25 when an ultrasonic wave U emitted from the ultrasonic transducer 25 is irradiated to the region to be inspected (called inspection region or inspected region, hereinafter) 28 of the inspection object 14.

The signal processing section 20 applies a parallel arithmetic processing to the electric signal dependent on reflected echo detected by the signal detecting circuit 19 and produces ultrasonic image data (image data). The signal processing section 20 includes amplifiers $31a$, $31b$, ... $31i$ for amplifying the electric signal dependent on reflected echo detected by the signal detecting circuit 19, A/D converters $32a$, $32b$, ... $32i$ for converting the amplified electric signal dependent on reflected echo from an analog signal to a digital signal, parallel processors $33a$, $33b$, ... $33i$ for producing ultrasonic image data obtained by visualizing the internal condition of the inspection object 14 based on the electric signal dependent on the reflected echo converted into the digital signal, and an integration processor 34 for producing integrated ultrasonic image data obtained by integrating multiple pieces of ultrasonic image data produced by the parallel processors $33a$, $33b$, ... $33i$.

The first display unit 21 and a second display unit 36 are each composed of a display section, an arithmetic section, a memory section and the like, and produce and display a required image based on the ultrasonic image data processed by the signal processing section 20.

Further, the first display unit 21 and the second display unit 36 perform comparison processing with preliminarily input threshold values, respectively, and when an abnormal value is detected, the abnormality is displayed.

The control circuit 22 controls the operation of the signal generator 17, the drive element selecting section 18, the signal detecting circuit 19, the signal processing section 20, the first display unit 21 and the second display unit 36, and controls the sequential operations including emission, reception, visualization and displaying of ultrasonic wave.

Upon receipt of an inspection start command from the first input unit 23, the control circuit 22 first instructs the signal generator 17 to produce a signal of driving the ultrasonic transducer 25 for the purpose of producing integrated ultrasonic image data on the inspection region 28 of the inspection object 14. Further, in order to select the piezoelectric vibrator 26 to which the drive signal is to be supplied from the multiple piezoelectric vibrator 26 constituting the ultrasonic transducer 25, the control circuit 22 instructs the drive element selecting section 18 to select a piezoelectric vibrator 26 to which the drive signal is to be supplied.

After the piezoelectric vibrator 26 has been driven, ultrasonic wave U is transmitted to the inspection region 28 of the inspection object 14, and a reflected echo dependent on the ultrasonic wave U is received by the piezoelectric vibrator 26 and converted into an electric signal. Although this reflected echo is received simultaneously by the multiple piezoelectric vibrators 26, since the control circuit 22 instructs the signal detecting circuit 19 to select a piezoelectric vibrator 26, the reflected echo needed to produce ultrasonic image data is selected.

Further, the control circuit 22 instructs the signal processing section 20 to perform a series of processes of amplifying, A/D converting and visualizing an electric signal dependent on reflected echo in order to amplify the electric signal dependent on reflected echo based on the ultrasonic wave U, to A/D convert the signal and to create integrated ultrasonic image data of (i.e., visualize) the signal by the parallel processors and the integration processor.

Furthermore, the control circuit 22 sends a control command for displaying the visualized data on the first display unit 21.

A command to start or terminate an inspection or to switch images, or a command to set inspection conditions is input to the control circuit 22 through the first input unit 23, thereby performing the operation of the ultrasonic inspection apparatus 10.

The ultrasonic probe apparatus 12 constituting the ultrasonic inspection apparatus 10 includes: the ultrasonic transducer 25 which sends or receives ultrasonic wave U; the second display unit 36; and a second input unit 37 used to input to the control circuit 22 included in the apparatus body 11, an operation input such as a command to start or terminate an inspection or a command to set inspection conditions so as to operate the ultrasonic inspection apparatus 10, and the above units of the ultrasonic probe apparatus 12 are integrally arranged within a probe holder 38. Furthermore, the control circuit 22 included in the apparatus body 11 sends, to the second display unit 36, a control command for displaying the integrated ultrasonic image data.

The ultrasonic transducer 25 includes a piezoelectric transducer section 39 in which multiple piezoelectric vibrators 26 acting as a piezoelectric transducer element are arranged in a matrix (m rows by n columns), and the piezoelectric transducer section 39 constitutes an ultrasonic sensor as a matrix sensor. In the piezoelectric transducer section 39, the piezoelectric vibrators 26 may be arranged not in a matrix but in a shape of line or cross line (array-shaped) so that an array sensor is constructed. The ultrasonic sensor constituting the ultrasonic transducer 25 may be a matrix sensor or an array sensor.

A drive signal produced by the signal generator 17 is selectively applied to each of the piezoelectric vibrators 26 of the ultrasonic transducer 25 by the drive element selecting section 18. Based on the selection made by the drive element selecting section 18, the order of driving each of the piezoelectric vibrators 26 is determined with respect to one vibrator or multiple vibrators at a time, and each of the piezoelectric vibrators 26 is driven at a required drive timing to transmit an ultrasonic wave U.

The ultrasonic wave U emitted from each of the piezoelectric vibrators 26 irradiates the inspection region 28 of the inspection object 14, and the ultrasonic wave U is partly reflected on a density boundary layer of the inspection region 28 to form a reflected echo. The reflected echo is received by the ultrasonic transducer 25 (i.e., matrix sensor), which is the ultrasonic sensor.

In the ultrasonic transducer 25, a shoe member 40 being a liquid or solid acoustic propagation medium is brought into close contact with a transmission (emission)/reception surface as an ultrasonic sensor surface, more specifically, to the side of the inspection object 14. A couplant 41 for achieving acoustic matching of the ultrasonic wave U is arranged between the shoe member 40 and the inspection object 14. The couplant 41 is formed of gelled liquid having a low volatility. In the case of the shoe member 40 as an acoustic propagation medium being a liquid, there is no need for locating the couplant 41.

The shoe member 40 entirely has a box-shape having an opening area of the shoe member 40 set according to the size of the inspection region 28 of the inspection object 14, and the height of the shoe member 40 as an acoustic propagation medium is determined by the emission angle (spreading angle) of the ultrasonic waves transmitted from the piezoelectric vibrator 26.

The interior of the inspection region 28 of the inspection object 14 is subjected to the nondestructive inspection by using the ultrasonic wave U transmitted from the ultrasonic inspection apparatus 10. The inspection object 14 may be a multilayer structure obtained by stacking two or more plate-like structures, or may be a metal material or a plastic material.

In the signal generator 17 which makes a drive signal act on the ultrasonic transducer 25, a pulsed or continuous drive signal is produced by applying an external voltage so as to produce the ultrasonic waves by driving the piezoelectric substance of the piezoelectric vibrator 26. When the piezoelectric transducer section 39 is driven by the drive element selecting section 18 and a piezoelectric vibrator 26 of the i-th column and j-th row is selected, the drive signal is applied at a required timing to the selected piezoelectric vibrator 26 of the i-th column and j-th row. The drive element selecting section 18 sequentially selects, at a required timing, one or multiple piezoelectric vibrators 26 to be driven, and when a drive signal from the signal generator 17 is applied to the selected piezoelectric vibrator 26, the ultrasonic wave U is transmitted from the piezoelectric vibrator 26 onto the object to be inspected 14.

In a case where the ultrasonic transducer 25 (matrix sensor) has the piezoelectric vibrators 26 of m columns and n rows, for example, 10 by 10, one hundred piezoelectric vibrators 26 are arranged in a matrix in a plane (two dimensions), and each of the piezoelectric vibrators 26$ij$ (i=1 to 10, j=1 to 10) is sequentially driven by the drive element selecting section 18. When a drive signal is sequentially applied to each of the piezoelectric vibrators 26, the ultrasonic wave U is sequentially emitted from each of the piezoelectric vibrators 26 at that timing. Reflected echoes of the ultrasonic waves sequentially emitted from each of the piezoelectric vibrators 26 are sequentially received by the ultrasonic transducer 25, and the reflected echo, that is, the received signal is sent as an electric signal (electric echo signal) via the signal cable 13 to the signal detecting circuit 19.

The ultrasonic wave U sequentially transmitted from each of the piezoelectric vibrators 26 of the ultrasonic transducer 25 passes through the shoe member 40 acting as an acoustic propagation medium and then through the couplant 41, and is incident on the inner side of the inspection region 28 of the inspection object 14 and reflected on each of the boundary layers of the inspection region 28.

The reflected echoes (indicated by the upward broken-line arrows in FIG. 1) of the ultrasonic waves reflected on each of the boundary layers including the front surface 14$a$, the boundary surface, the bottom surface 14$b$, the internal flaw 42 and the like of the inspection object 14 go out of the inspection (inspected) object 14 and pass through the shoe member 40, and are each received at a different timing by each of the piezoelectric vibrators 26 of the ultrasonic transducer 25 and cause each of the piezoelectric vibrators 26 to vibrate, whereby the reflected echo is converted into an electric signal (electric echo signal). Subsequently, the electric echo signal is received via the signal cable 13 by the signal detecting circuit 19 and detected by each of the piezoelectric vibrators 26.

The signal detecting circuit 19 is connected in parallel via the signal cable 13 to each of the piezoelectric vibrators 26 of the ultrasonic transducer 25, and electric echo signals produced by the piezoelectric vibrators 26 of the piezoelectric transducer section 39 are guided via the signal cable 13 to the signal detecting circuit 19. Furthermore, by using the signal cable 13, drive signals from the signal generator 17 are guided via the drive element selecting section 18 to the piezoelectric vibrators 26 of the piezoelectric transducer section 39, respectively.

In the ultrasonic inspection apparatus 10, when a drive signal is applied to a piezoelectric vibrator 26 of the m-th column and n-th row in each of the piezoelectric vibrators 26 of the ultrasonic transducer 25, the piezoelectric vibrator 26 is started up to act as a piezoelectric substance for producing the ultrasonic wave and emits the ultrasonic wave U. The emitted ultrasonic wave U irradiates the inspection region 28 of the object to be inspected through the shoe member 40 and the couplant 41. The ultrasonic wave with which the inspection region 28 of the inspection object 14 is scanned is partly reflected on the density boundary layer of the inspection region 28 and makes reflected echoes. The reflected echoes pass through the couplant 41 and the shoe member 40, and are returned to the ultrasonic transducer 25 (matrix sensor) and received at a different timing by the piezoelectric vibrators 26, respectively. The piezoelectric vibrator 26 applies piezoelectric conversion to the reflected echo and produces an electric signal (electric echo signal). The electric echo signal is sent via the signal cable 13 to the signal detecting circuit 19 by which the electric echo signal is detected. The signal detecting circuit 19 is a circuit for detecting an electric signal dependent on the reflected echo produced by the ultrasonic transducer 25.

A plurality of electric echo signals of the electric echo signals detected by the signal detecting circuit 19 for the inspection are guided to the respective amplifiers 31$a$, 31$b$, . . . 31$i$ constituting the signal processing section 20.

The amplifiers 31$a$, 31$b$, . . . 31$i$ amplify the guided electric echo signals and supply the resultant signals to the A/D converters 32$a$, 32$b$, . . . 32$i$ of the signal processing section 20. The A/D converters 32$a$, 32$b$, . . . 32$i$ convert the amplified electric echo signals from analog signals to digital signals and guide them as the digital echo signals to the parallel processors 33$a$, 33$b$, . . . 33$i$ of the signal processing section 20. The parallel processors 33$a$, 33$b$, . . . 33$i$ process the digital echo signals supplied from the A/D converters 32$a$, 32$b$, . . . 32$i$ and thereby produce ultrasonic image data obtained by visualizing the internal state of the inspection (inspected) object 14. Multiple pieces of ultrasonic image data produced by the parallel processors 33$a$, 33$b$, . . . 33$i$ are integrated by the integration processor 34 to produce integrated ultrasonic image data. The integrated ultrasonic image data is supplied to the first display unit 21.

In a case where a multiplexer (not illustrated) is mounted on the signal detecting circuit 19 or the signal processing section 20, there is no need for multiple parallel processors 33a, 33b, . . . 33i and the integration processor 34, and a single parallel processor can produce the integrated ultrasonic image data.

The integrated ultrasonic image data, produced by processing the digitized reflected echo (digital echo signal) in the signal processing section 20, is sent to the first display unit 21, in which the integrated ultrasonic image data is subjected to visualization processing and displayed as an image.

On the other hand, in the ultrasonic probe apparatus 12, the second display unit 36 is arranged integrally with the ultrasonic transducer 25 within the probe holder 38. The integrated ultrasonic image data, produced by processing the digitized ultrasonic echo signal in the signal processing section 20, is also sent to the second display unit 36, in which the integrated ultrasonic image data is subjected to visualization processing and displayed as an image.

For the second display unit 36, a liquid crystal display, an LED (Light Emitting Diode), an EL (Electro Luminescence), a VFD (Vacuum Fluorescent Display), a PDP (Plasma Display Panel) or the like may be used.

The first display unit 21 and the second display unit 36 receive from the signal processing section 20, the integrated ultrasonic image data produced according to a command input from the first input unit 23 or the second input unit 37, and can thus display an ultrasonic image obtained by visualizing the internal state of the inspection object 14 based on a control signal generated from the control circuit 22.

The ultrasonic images displayed in the first display unit 21 and the second display unit 36 are produced by at least one image selected from: a reflected echo waveform image (A scope or A scan) of ultrasonic wave U in the inspection region 28 of the inspection object 14; a cross-sectional image (B scope or B scan) in the inspection region 28 of the inspection object 14; a two-dimensional image (C scope or C scan) of reflected echo peak value of ultrasonic wave U in the inspection region 28 of the inspection object 14; a two-dimensional image (D scope or D scan) of reflected echo depth of ultrasonic wave U in the inspection region 28 of the inspection object 14; and information or data as the result of extracting and calculating reflected echo data (front surface, flaw, bottom surface) of ultrasonic wave U in the inspection region 28 of the inspected object 14.

By checking the peak position of the reflected echo waveform image (A scope or A scan) of ultrasonic wave U in the inspection region 28 of the inspection object 14 displayed in the second display unit 36, the front surface 14a, the internal flaw 42 or the bottom surface 14b in the inspection region 28 of the inspection object 14 can be checked at the side of the ultrasonic probe apparatus 12.

Further, from the cross-sectional image (B scope or B scan) in the inspection region 28 of the inspection object 14 displayed in the second display unit 36, it can be checked at the side of the ultrasonic probe apparatus 12 whether or not the ultrasonic transducer 25 properly faces an inspected surface in the inspection region 28 of the inspection object 14, or the front surface 14a, the internal flaw 42 or the bottom surface 14b in the inspection region 28 of the inspection object 14 can be checked at the side of the ultrasonic probe apparatus 12.

Furthermore, from the two-dimensional image (C scope or C scan) of reflected echo peak value of ultrasonic wave U in the inspection region 28 of the inspection object 14 displayed in the second display unit 36, the two-dimensional image of echo intensity in the inspection region 28 of the inspection object 14 can be checked at the side of the ultrasonic probe apparatus 12.

Still furthermore, from the two-dimensional image (D scope or D scan) of reflected echo depth of ultrasonic wave U in the inspection region 28 of the inspection object 14 displayed in the second display unit 36, the two-dimensional image of depth information in the inspection region 28 of the inspection object 14 can be checked at the side of the ultrasonic probe apparatus 12.

From the information or data as the result of extracting and calculating the reflected echo data (front surface 14a, internal flaw 42, bottom surface 14b) of the ultrasonic wave U in the inspection region 28 of the inspection object 14 displayed in the second display unit 36, various pieces of data on the size, the position and the like of the flaw in the inspection region 28 of the inspection object 14 can be checked at the side of the ultrasonic probe apparatus 12.

The second input unit 37 is constituted of, for example, a push button switch having a toggle function. In this case, the inspection by the ultrasonic inspection apparatus 10 is initiated by a first depression of the button, and the inspection by the ultrasonic inspection apparatus 10 is terminated by a second depression of the button and thereby the basic operation of the ultrasonic inspection apparatus 10 can be performed by manipulating the single push button. Further, the second input unit 37 includes, for example, a selection switch having a toggle function, and ultrasonic images displayed in the second display unit 36 can be sequentially switched by using the selection switch. Furthermore, the second input unit 37 includes, for example, a pair of push button switches constituted of an addition switch and a subtraction switch.

In the second input unit 37, an inspection condition setting input is performed through the pair of push button switches. Examples of inspection-condition setting include: gain setting of the ultrasonic transducer 25; setting of the number of samplings used in averaging digital echo signals used to produce ultrasonic image data; and adjustment of visualization start position in producing a cross-sectional image (B scope or B scan) in the inspection region 28 of the inspection object 14.

In the second input unit 37, setting values of the inspection conditions are added or subtracted by using the pair of push button switches, thereby performing the inspection condition setting input.

The ultrasonic probe apparatus 12 includes the second display unit 36 and the second input unit 37, and accordingly, in performing non-destructive inspection by the ultrasonic inspection apparatus 10, the checking of ultrasonic images and the manipulation of the ultrasonic inspection apparatus 10 can be continuously performed in the ultrasonic probe apparatus 12 with the ultrasonic transducer 25. The operator (inspector) can inspect the object 14 by paying attention only to the ultrasonic probe apparatus 12.

Figure 2A:
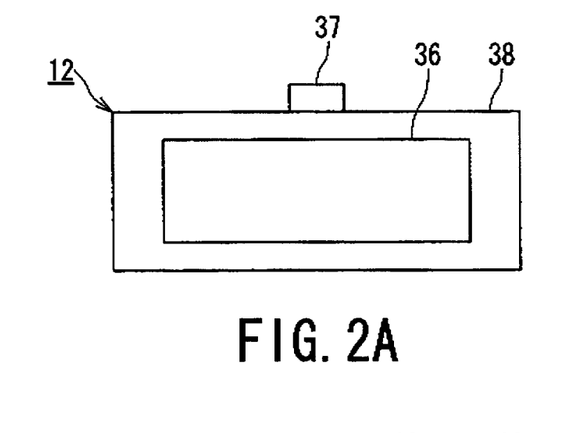
Figure 2B:
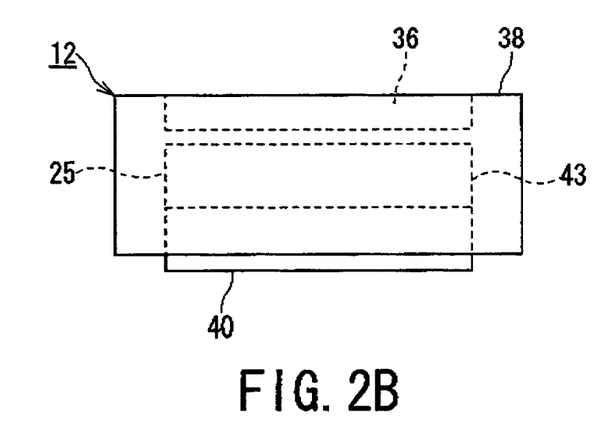
Figure 2C:
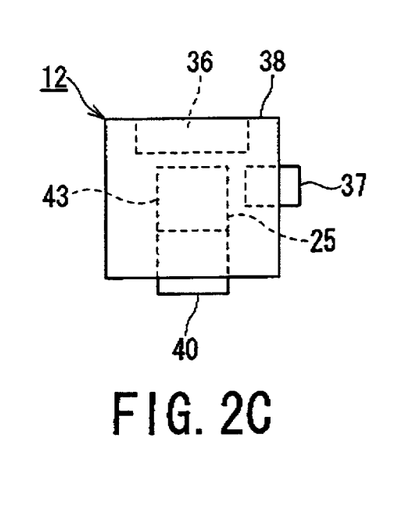

FIG. 2 is a view schematically illustrating one example of a configuration of a probe holder constituting the ultrasonic probe apparatus of the ultrasonic inspection apparatus according to the present invention, in which FIG. 2 (A) is a plan view, FIG. 2 (B) is a front view, and FIG. 2 (C) is a side view.

The probe holder 38 has, as illustrated in FIGS. 2 (A), (B) and (C), a box-shape, in which an ultrasonic sensor holder chamber 43 is formed which has an opening opened in a direction of radiating the ultrasonic wave U on the inspection object (object to be inspected) 14 (in a downward direction in the probe holder 38 according to the present embodiment). The ultrasonic transducer 25 is contained in the ultrasonic sensor holder chamber 43 so that the ultrasonic sensor surface of the ultrasonic transducer 25 faces a direction of radiating the ultrasonic wave U on the inspection object 14 (in a downward direction in the probe holder 38 according to the present embodiment). Further, the shoe member 40 is arranged between the ultrasonic sensor surface of the ultrasonic transducer 25 contained in the ultrasonic sensor holder chamber 43 and the surface (lower surface) of the probe holder 38 oriented to the inspection object 14. The shoe member 40 is arranged so as to protrude from the lower surface of the probe holder 38, and when the ultrasonic probe apparatus 12 is manipulated over the inspection object 14, the shoe member 40 comes into contact with the inspection object 14 earlier than the lower surface of the probe holder 38. The opening area of the shoe member 40 is set according to the size of the inspection region 28 of the inspection object 14, and the height of the shoe member 40 is determined by the emission angle (spreading angle) of ultrasonic waves emitted from the piezoelectric vibrator 26. Thus, the opening area and the height of the ultrasonic sensor holder chamber 43 are set to a required value based on the opening area and the height of the shoe member 40 and on the size of the ultrasonic transducer 25.

Further, the second display unit 36 is arranged on the upper surface of the probe holder 38. In manipulating the ultrasonic probe apparatus 12 over the inspection object 14, the operator (inspector) of the ultrasonic probe apparatus 12 can easily manipulate the ultrasonic probe apparatus 12 while checking an ultrasonic image obtained by visualizing the internal state of the inspection object 14 by using the second display unit 36.

Furthermore, the second input unit 37 is arranged on the back surface of the probe holder 38. In manipulating the ultrasonic probe apparatus 12 over the inspection object 14, the operator (inspector) of the ultrasonic probe apparatus 12 can manipulate the ultrasonic inspection apparatus 10 while checking an ultrasonic image obtained by visualizing the internal state of the inspection object 14 by using the second display unit 36 and also inputting a command to start or terminate an inspection or a command to set inspection conditions through the second input unit 37.

The probe holder 38 may be formed by optimizing, based on the shape of the inspection object 14 and the direction of an inspected surface of the inspection object 14 during inspection when the probe holder 38 is used, the opening direction of the ultrasonic sensor holder chamber 43 in the probe holder 38 and the structure of the surfaces on which the second display unit 36 and the second input unit 37 are arranged.

Hereunder, an ultrasonic inspection method using the ultrasonic inspection apparatus 10 according to the present embodiment will be described.

Figure 3:
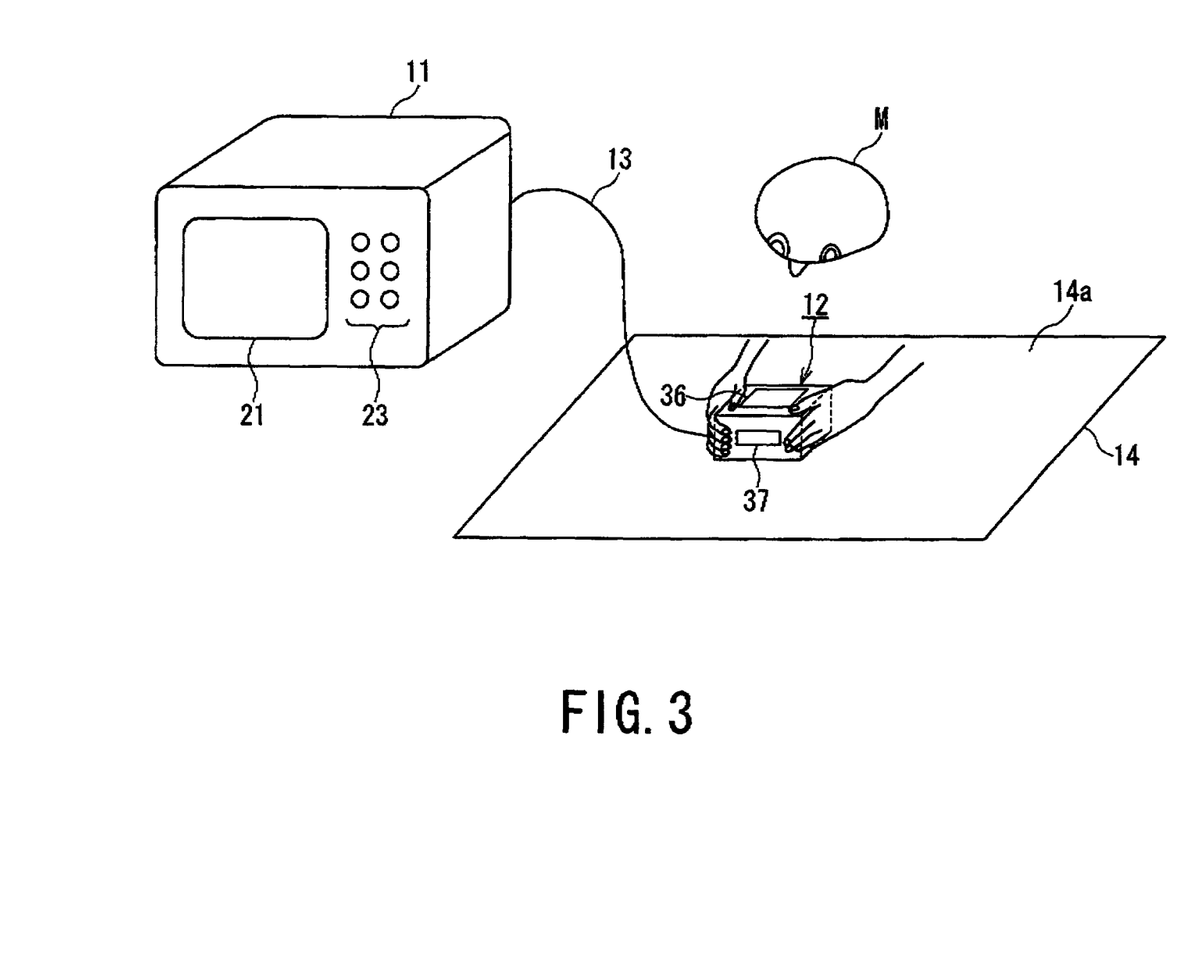
FIG. 3 is a schematic view showing a condition of an ultrasonic inspection method using the ultrasonic inspection apparatus according to the present invention.

FIG. 3 is a schematic view showing an ultrasonic inspection method in the use of the ultrasonic inspection apparatus according to the present invention.

In performing an ultrasonic inspection of an inspection object (object to be inspected) 14 by using the ultrasonic inspection apparatus 10, as illustrated in FIG. 3, an operator (inspector) M first places the ultrasonic inspection apparatus 10 around the inspection object 14 or places the inspection object 14 in the vicinity of the ultrasonic inspection apparatus 10.

Figure 4:
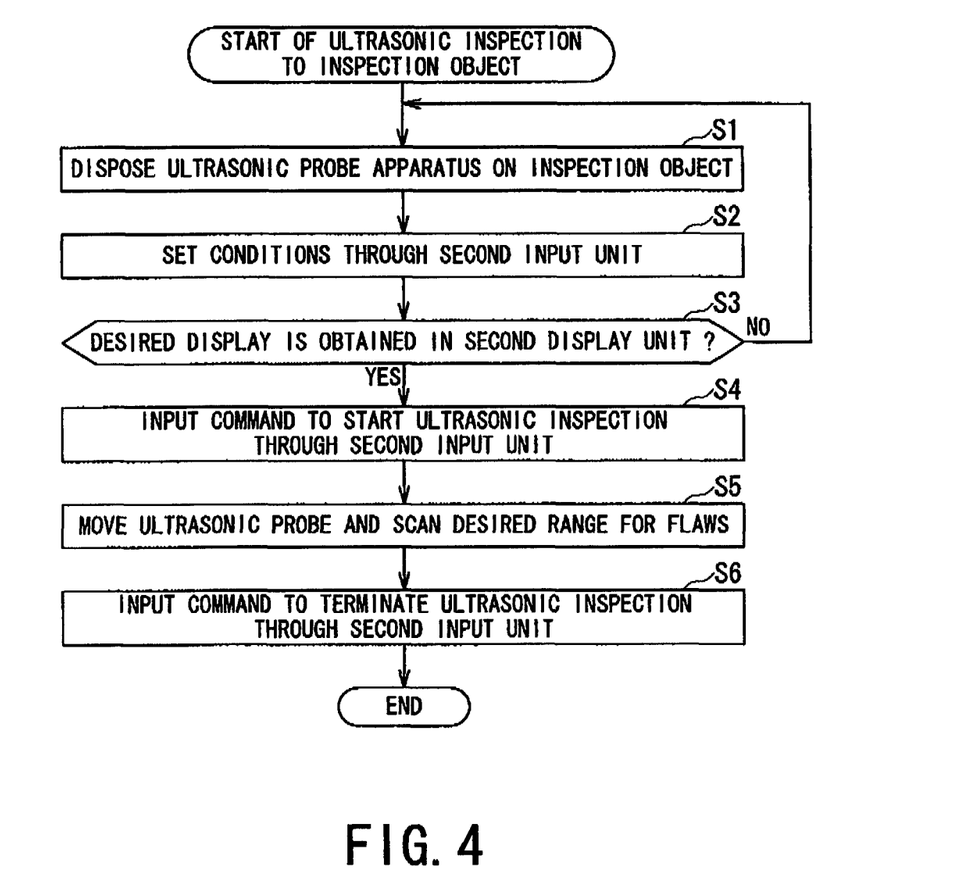
FIG. 4 is a flowchart illustrating an example of ultrasonic inspection method using the ultrasonic inspection apparatus according to the present invention.

FIG. 4 is a flowchart illustrating an example of ultrasonic inspection method using the ultrasonic inspection apparatus according to the present invention.

First, in step S1, as shown in FIG. 4, the operator (inspector) M places the ultrasonic probe apparatus 12 constituting the ultrasonic inspection apparatus 10 at a desired inspection position of the inspection object 14. More specifically, the operator M holds the probe holder 38 of the ultrasonic probe apparatus 12 by the hands and places the ultrasonic probe apparatus 12 at a desired inspection position with the lower surface of the probe holder 38 oriented to the inspection object 14.

Subsequently, in step S2, the operator (inspector) M performs an inspection condition setting input through a pair of push button switches constituted of an addition switch and a subtraction switch of the second input unit 37. More specifically, while holding the probe holder 38 of the ultrasonic probe apparatus 12 by the hands, the operator M manipulates the addition switch and the subtraction switch of the second input unit 37 to set, for example, the gain of the ultrasonic transducer 25, the number of samplings used in averaging digital echo signals used to produce ultrasonic image data, or adjusts the visualization start position in producing a cross-sectional image (B scope or B scan) in the inspection region 28 of the inspection object 14.

Subsequently, in step S3, the operator (inspector) M views the second display unit 36 and determines whether or not a desired display has been obtained and adjusts the inspection conditions. When a desired display has been obtained, the operation proceeds to step S4. Otherwise, the operation returns to step S1, and steps S1 to S3 are repeated to adjust the inspection conditions. In this case, the operator (inspector) M manipulates the selection switch of the second input unit 37 and sequentially switches ultrasonic images displayed in the second display unit 36 and determines whether or not a desired display has been obtained. This determination of whether or not a desired display has been obtained is carried by displaying, on the second display unit 36, a reflected echo waveform image (A scope or A scan) of ultrasonic wave U in the inspection region 28 of the inspection object 14 or a cross-sectional image (B scope or B scan) in the inspection region 28 of the inspection object 14.

Still subsequently, in step S4, the operator (inspector) M manipulates the push button switch of the second input unit 37 to input an ultrasonic inspection start command.

Subsequently, in step S5, the operator (inspector) M moves the ultrasonic probe apparatus 12 in a desired range of the inspection object 14 while viewing the second display unit 36 to thereby inspect and scan the inspection region 28. More specifically, the operator M causes the ultrasonic probe apparatus 12 to scan a surface 14a of the inspection object 14 in a desired range of the inspection object 14 while holding the probe holder 38 of the ultrasonic probe apparatus 12 by the hands, and checks on the presence or absence of an internal flaw 42 while viewing the ultrasonic images displayed in the second display unit 36.

Subsequently, in step S6, after finishing the inspection of the desired range of the inspection object 14, the operator (inspector) M manipulates the push button switch of the second input unit 37 to input an ultrasonic inspection terminating command.

The ultrasonic inspection apparatus 10 functions as an ultrasonic camera provided with the ultrasonic sensor, ultrasonic waveforms of several thousands to several tens of thousands of reflected echoes can be instantaneously collected, and an image combination process allows implementation of a parallel arithmetic process for visualizing, at a high speed, the internal flaw 42 of the inspection object 14 (the state of junction regions, or the presence/absence or the state of welding flaws).

Furthermore, in the ultrasonic inspection apparatus 10, the internal structure of the inspection object 14 can be quickly extracted and displayed as a two or three dimensional highly-sensitive, high-resolution ultrasonic image, and a high-speed inspection of one second to several tens of seconds per image can thus be implemented.

The ultrasonic inspection apparatus 10 and the ultrasonic inspection method using the ultrasonic inspection apparatus 10 can be applied to the inspection of the maintenance state of welding parts or presence/absence of welding flaws in the fields of automobile, airplane and railway, or to the monitoring of the state of the welding parts in industrial fields of plant, shipbuilding and the like.

In the ultrasonic inspection apparatus 10 according to the present embodiment, the ultrasonic probe apparatus 12 is electrically connected to the apparatus body 11 via a flexible signal cable 13, and in the ultrasonic probe apparatus 12, the ultrasonic transducer 25, the second display unit 36 and the second input unit 37 are integrally contained within the probe holder 38 of a palm size. As a result, the ultrasonic images obtained by visualizing the internal state of the inspection object 14 can be checked using the second display unit 36 while manually operating the ultrasonic probe apparatus 12 in an easy and simple manner along the surface of the inspection object 14. That is, the operator (inspector) M using the ultrasonic inspection apparatus 10 can perform an ultrasonic inspection by paying attention only to the ultrasonic transducer 25 without watching another apparatus, thus facilitating the inspection performance.

Furthermore, since the ultrasonic transducer 25, the second display unit 36 and the second input unit 37 are integrally contained within the probe holder 38 included in the ultrasonic probe apparatus 12, the variation or change of the ultrasonic images obtained by causing the ultrasonic transducer 25 to scan over the inspection object 14 and visualizing the internal state of the inspection object 14 can be checked in real-time by way of the ultrasonic images sent from the signal processing section 20 and displayed in the second display unit 36. Accordingly, the operator (inspector) M using the ultrasonic inspection apparatus 10 can instantaneously check the internal flaw 42 (peel-off, void or the like) or the internal state such as an unstuck state of a junction of the inspection object 14 without changing the operator's line of sight and can also perform the inspection while feeding back the state of ultrasonic images.

Still furthermore, since the ultrasonic transducer 25, the second display unit 36 and the second input unit 37 are integrally contained within the probe holder 38, by using the ultrasonic images sent from the signal processing section 20 and displayed in the second display unit 36, the operator (inspector) M can manipulate the ultrasonic inspection apparatus 10 through the second input unit 37 while checking in real-time variation or change of the ultrasonic images obtained by causing the ultrasonic transducer 25 to scan over the inspection object 14 and thereby visualizing the internal state of the inspection object 14. Accordingly, the operator (inspector) M using the ultrasonic inspection apparatus 10 can instantaneously check the internal flaw 42 (peel-off, void or the like) or the internal state such as an unstuck state of a junction of the inspection object 14 without changing the operator's line of sight, and the operator can also manipulate the ultrasonic inspection apparatus 10 to perform the inspection while feeding back the state of ultrasonic images.

Still furthermore, the second display unit 36 using a display method appropriate for the purpose of the inspection of the inspection object 14, the shape of the probe holder 38, or the like is provided, and data useful for the inspection are collectively displayed, so that the inspection can be significantly simplified and facilitated.

According to the ultrasonic inspection apparatus 10, the ultrasonic transducer 25 and the ultrasonic inspection method using the ultrasonic inspection apparatus 10, the internal flaw 42 (peel-off, void or the like) or the internal state such as an unstuck state of a junction of the object to be inspected 14 can be inspected efficiently and accurately by easy manipulation in the field or the manufacturing process site.

The invention claimed is:

1. An ultrasonic inspection apparatus comprising:
an ultrasonic probe apparatus comprising
an ultrasonic transducer comprising a plurality of piezoelectric vibrators for
generating an ultrasonic wave,
receiving an ultrasonic echo reflected from an inspection object, and
generating an electric echo signal corresponding to the ultrasonic echo;
a display unit; and
a switch configured to receive at least one of an inspection-starting command or an inspection-terminating command;
a drive element selecting section, connected to the plurality of piezoelectric vibrators, to select a piezoelectric vibrator based on a drive signal from a signal generator;
a signal detecting circuit connected to receive the electric echo signal; and
a signal processing section to:
apply a parallel arithmetic process to the received electric echo signal;
produce, from the electric echo signal, image data corresponding to an internal image of the inspection object; and
supply the image data to the display unit for display of the internal image of the inspection object;
wherein the display unit is configured to display that the ultrasonic transducer properly faces an inspected surface in an inspection region by a cross-sectional image in the inspection region of at least the inspection object as an image based on the internal image of the inspection object produced in the signal processing unit, and
wherein the switch is configured to set the inspection condition including the inspection-starting command, the inspection terminating command, and a position adjustment of an image-starting-position at a time of producing the cross-sectional image.

2. The ultrasonic inspection apparatus according to claim 1, wherein the image displayed in the display unit includes an echo waveform image of the reflected echo from the inspection object.

3. The ultrasonic inspection apparatus according to claim 1, wherein the image displayed in the display unit includes a cross-sectional image of the inspection object.

4. The ultrasonic inspection apparatus according to claim 1, wherein the image displayed in the display unit includes an image produced by extracting an echo peak value in a depth direction of the inspection object.

5. The ultrasonic inspection apparatus according to claim 1, wherein the image displayed in the display unit includes an image produced by extracting depth data of the reflected echo from the inspection object.

6. The ultrasonic inspection apparatus according to claim 1, wherein the image displayed in the display unit includes a display of a result of extracting data on the inspection object from the reflected echo from the inspection object and then performing an arithmetical operation on the data.

7. An ultrasonic probe apparatus connected to a main body of an ultrasonic inspection apparatus, comprising:
a probe holder in a shape of a box;
an ultrasonic transducer including a plurality of piezoelectric vibrators incorporated in the probe holder;
a display unit incorporated in the probe holder; and
a switch incorporated in the probe holder, the switch being configured to receive at least one of an inspection-starting command or an inspection-terminating command, wherein the ultrasonic transducer, the display unit, and the switch are integrally assembled within the probe holder;

wherein the display unit is configured to display that the ultrasonic transducer properly faces an inspected surface in an inspection region by a cross-sectional image in the inspection region of at least the inspection object as an image based on the internal image of the inspection object produced in the signal processing unit, and wherein the switch is configured to set the inspection condition including the inspection-starting command, the inspection-terminating command, and a position adjustment of an image-starting-position at a time of producing the cross-sectional image.

8. The ultrasonic probe apparatus according to claim 7, wherein an image displayed in the display unit includes an echo waveform image of a reflected echo from an inspection object.

9. The ultrasonic probe apparatus according to claim 7, wherein the image displayed in the display unit includes a cross-sectional image of the inspection object.

10. The ultrasonic probe apparatus according to claim 7, wherein the image displayed in the display unit includes an image produced by extracting an echo peak value in a depth direction of the inspection object.

11. The ultrasonic probe apparatus according to claim 7, wherein the image displayed in the display unit includes an image produced by extracting depth data of the reflected echo from the inspection object.

12. The ultrasonic probe apparatus according to claim 7, wherein the image displayed in the display unit includes a display of a result of extracting data on the inspection object from the reflected echo from the inspection object and then performing an arithmetical operation on the data.

13. An ultrasonic inspection method comprising the steps of:

preparing an ultrasonic inspection apparatus comprising:
an ultrasonic probe apparatus comprising:
an ultrasonic transducer comprising a plurality of piezoelectric vibrators for generating an ultrasonic wave, receiving an ultrasonic echo reflected from an inspection object, and generating an electric echo signal corresponding to the ultrasonic echo;
a display unit configured to display that the ultrasonic transducer properly faces an inspected surface in an inspection region by a cross-sectional image in the inspection region of at least the inspection object as an image based on the internal image of the inspection object produced in the signal processing unit; and
a switch configured to receive at least one of an inspection-starting command, an inspection-terminating command, or an inspection-condition-setting command, and set the inspection condition including the inspection-starting command, the inspection-terminating command and position adjustment of image-starting-position at a time of producing the cross-sectional image;
a drive element selecting section connected to the plurality of piezoelectric vibrators and selecting a piezoelectric vibrator based on a drive signal from a signal generator;
a signal detecting circuit receiving the electric echo signal; and
a signal processing section which:
applies a parallel arithmetic process to the received electric echo signal;
produces, from the electric echo signal, image data corresponding to an internal image of the inspection object; and
supplies the image data to the display unit for display of the internal image of the inspection object;
disposing the ultrasonic probe apparatus at a predetermined inspection position of the inspection object;
inputting the inspection-condition-setting command to set inspection conditions through the switch;
repeating the disposing of the ultrasonic probe apparatus and the inputting of the inspection-condition-setting command until a predetermined display is obtained in the display unit;
inputting the inspection-starting command through the switch after the predetermined display is obtained;
inspecting the inspection object for flaws by causing the ultrasonic probe apparatus to scan a predetermined range of the inspection object; and
inputting the inspection-terminating command through the switch after the inspecting the predetermined range of the inspection object is completed.

14. The ultrasonic inspection method according to claim 13, wherein at least one of inputting the inspection-condition-setting command, inputting the inspection-starting command, or inputting the inspection-terminating command through the switch is performed with the ultrasonic probe apparatus being held.

15. The ultrasonic inspection method according to claim 13, wherein inputting the inspection-condition-setting command is performed after displaying, in the display unit, an echo waveform image of the reflected echo from the inspection object, or a cross-sectional image of the inspection object.

* * * * *